US009078966B2

(12) United States Patent
Bruce

(10) Patent No.: US 9,078,966 B2
(45) Date of Patent: Jul. 14, 2015

(54) PUSH TO INSTALL SYRINGE MOUNT FOR POWERED INJECTOR SYSTEMS

(75) Inventor: John K. Bruce, Burlington, KY (US)

(73) Assignee: LIEBEL-FLARSHEIM COMPANY LLC, Hazelwood, MO (US)

( * ) Notice: Subject to any disclaimer, the term of this patent is extended or adjusted under 35 U.S.C. 154(b) by 705 days.

(21) Appl. No.: 12/746,192

(22) PCT Filed: Dec. 2, 2008

(86) PCT No.: PCT/US2008/085239
§ 371 (c)(1),
(2), (4) Date: Jun. 4, 2010

(87) PCT Pub. No.: WO2009/073650
PCT Pub. Date: Jun. 11, 2009

(65) Prior Publication Data
US 2010/0280369 A1 Nov. 4, 2010

Related U.S. Application Data

(60) Provisional application No. 61/012,095, filed on Dec. 7, 2007.

(51) Int. Cl.
*A61M 5/46* (2006.01)
*A61M 5/32* (2006.01)
*A61M 5/145* (2006.01)
*A61B 6/00* (2006.01)

(52) U.S. Cl.
CPC ............. *A61M 5/14546* (2013.01); *A61B 6/00* (2013.01); *A61M 5/14566* (2013.01); *A61M 5/32* (2013.01); *A61M 5/46* (2013.01)

(58) Field of Classification Search
CPC ............ A61B 6/00; A61M 5/32; A61M 5/30; A61M 5/31511; A61M 2005/2073; A61M 5/46
USPC .......................................................... 600/432
See application file for complete search history.

(56) References Cited

U.S. PATENT DOCUMENTS

| | | | |
|---|---|---|---|
| 5,383,858 A | 1/1995 | Reilly et al. |
| 5,535,746 A | 7/1996 | Hoover et al. |
| 5,865,805 A | 2/1999 | Ziemba |
| 5,997,502 A | 12/1999 | Reilly et al. |
| 6,090,064 A | 7/2000 | Reilly et al. |
| 6,279,569 B1 | 8/2001 | Berthon-Jones |
| 6,336,913 B1 | 1/2002 | Spohn et al. |
| 6,562,008 B1 | 5/2003 | Reilly et al. |
| 6,569,127 B1 | 5/2003 | Fago et al. |
| 6,585,700 B1 | 7/2003 | Trocki et al. |

(Continued)

FOREIGN PATENT DOCUMENTS

| | | |
|---|---|---|
| EP | 1 233 800 B1 | 7/2007 |
| JP | 2006230907 | 9/2006 |

(Continued)

*Primary Examiner* — Vani Gupta
(74) *Attorney, Agent, or Firm* — Marsh Fischmann & Breyfogle LLP

(57) ABSTRACT

Disclosed embodiments provide for a syringe mount of a power injector. The syringe mount may include a plurality of syringe retainer components that translate (e.g., move linearly without rotation) toward and away from a longitudinal axis of the injector drive ram. These retainer components may be biased (e.g., via a spring) toward one another and/or the longitudinal axis of the injector drive ram.

27 Claims, 7 Drawing Sheets

(56) References Cited

U.S. PATENT DOCUMENTS

| | | |
|---|---|---|
| 6,652,489 B2 | 11/2003 | Trocki et al. |
| 6,726,657 B1 | 4/2004 | Dedig et al. |
| 6,808,513 B2 | 10/2004 | Reilly et al. |
| 6,929,619 B2 | 8/2005 | Fago et al. |
| 6,958,053 B1 | 10/2005 | Reilly |
| 7,029,458 B2 | 4/2006 | Spohn et al. |
| 7,029,459 B2 | 4/2006 | Reilly |
| 2004/0024359 A1 | 2/2004 | Reilly et al. |
| 2004/0024361 A1 | 2/2004 | Fago et al. |
| 2004/0152979 A1 | 8/2004 | Sakakibara et al. |
| 2005/0113754 A1 | 5/2005 | Cowan |
| 2010/0286661 A1* | 11/2010 | Raday et al. .................. 604/520 |

FOREIGN PATENT DOCUMENTS

| | | |
|---|---|---|
| WO | WO 02/056945 A2 | 7/2002 |
| WO | 03101527 A1 | 12/2003 |

* cited by examiner

PUSH TO INSTALL SYRINGE MOUNT FOR POWERED INJECTOR SYSTEMS

RELATED APPLICATIONS

This application is a U.S. National Stage of PCT/US2008/085239 filed 2 Dec. 2008, which claims priority to and is a non-provisional application of U.S. Provisional Patent Application No. 61/012,095 filed on 7 Dec. 2007 and entitled "Push to Install Syringe Mount for Powered Injector Systems". Priority is claimed to each patent application set forth in this Related Applications section.

FIELD OF THE INVENTION

The invention relates generally to powered injectors for injecting medical fluids and, more specifically, to systems and methods for mounting syringes to such powered injectors.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Generally, a power injector is used to inject medical fluids, such as a pharmaceutical, radiopharmaceutical, or contrast media, into a patient. For example, the medical fluid may be disposed within a syringe, which in turn may be mounted onto the power injector. When injecting using one of these powered injectors to inject medical fluid into the patient, a ram disposed behind the mounted syringe may push the syringe's plunger, thereby forcing the fluid toward the tip of the syringe to inject the fluid into the patient. Unfortunately, existing power injectors may suffer from design shortcomings which may affect the manner by which syringes may be mounted onto and/or may be retained within a power injector. Such design inadequacies may lower overall quality and/or efficiency of the injection process. In addition, design shortcomings associated with power injectors may complicate the manner by which a user, such as a healthcare provider, administers an injection procedure.

SUMMARY

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

A first aspect of the present invention is directed to a front-loading, contrast media injector. This injector includes a drive ram and an injector housing, which has an opening defined therein. The injector is configured such that at least a portion of the drive ram is movable into and out of the injector housing along a longitudinal reference axis of the drive ram through the opening in the injector housing. The injector also includes a syringe mount that is coupled to the housing. This syringe mount includes a plurality of retainer components to assist in holding the syringe so that the injector can be utilized to expel an appropriate medical fluid (e.g., contrast media, saline, or a combination thereof) from the syringe. Each of the retainer components of the syringe mount includes a sloped (e.g., angled, slanted, tapered) surface that slopes toward a longitudinal axis of the drive ram. Moreover, each of the retainer components is designed to translate (e.g., relative to the housing) toward and away from the longitudinal axis but is biased toward the longitudinal reference axis. Incidentally, "biased" or the like herein means at least generally urged/forced in and/or toward a particular direction. For instance, in some embodiments, the retainer components may be biased toward the longitudinal reference axis of the drive ram due to spring forces imposed on each of the retainer components (e.g., spring-biased).

Various refinements exist of the features noted in relation to the first aspect of the present invention. Further features may also be incorporated in the first aspect of the present invention as well. These refinements and additional features may exist individually or in any combination. The following discussion pertains to this first aspect, up to the start of the discussion of a second aspect of the present invention.

The syringe mount may include any appropriate quantity of retainer components. For instance, in some embodiments, the syringe mount includes a first retainer component and a second retainer component (e.g., at least two retainer components). In such embodiments, the first and second retainer components may be oriented such that the longitudinal reference axis of the drive ram is interposed between and does not intersect either of the first and second retainer components.

The retainer components may exhibit any appropriate design as long as they at least assist in allowing a syringe to be mounted to the injector. Accordingly, a syringe may be located between at least two retainer components when the syringe is mounted on the syringe mount. In some embodiments, the retainer components (e.g., the first and second retainer components) may be C-clamps. Each of the retainer components may have a receptacle defined therein to accommodate at least a portion of a flange of a syringe.

The retainer components collectively may exhibit any appropriate positional relationship relative to one another. For instance, the retainer components may be oriented such that they collectively define at least a portion of a substantially conical aperture adapted to receive a syringe.

The sloped surface of each of the retainer components may be designed to cause translation of the retainer components outwardly away from the longitudinal reference axis of the drive ram when a syringe is moved along the longitudinal reference axis toward and/or into the opening in the injector housing.

The syringe mount of some embodiments may include a lock of sorts that is adapted to at least temporarily secure the retainer components in a desired (e.g., open or closed) position. This lock may exhibit any appropriate design. For instance, in some embodiments, the lock may include a lever. In such embodiments, the retainer components may be separated from one another by a first distance when the lever is in a first position. Further, the retainer components may be separated from one another by a second distance greater than the first distance when the lever is in a second position different from the first position.

The syringe mount may be coupled to the housing of the injector in any appropriate manner. Incidentally, "coupled" or the like herein refers to a condition of one thing being at least temporarily connected (either directly or indirectly) with another thing. As an example of an appropriate coupling of the syringe mount and the injector, the syringe mount may be a component of a removable face plate of the injector. As another example, the syringe mount may be substantially integral with the housing of the injector. As yet another example, the syringe mount may be a component of an adapter for at least temporarily making an original syringe mount of the injector compatible to accommodate a syringe that the original syringe mount was not originally designed to accommodate.

A second aspect of the invention is directed to a method of using a contrast media injector that includes a drive ram. At least a portion of the injectors drive ram is movable into and out of the injector along a longitudinal reference axis of the drive ram. In this method, a sloping surface of each of first and second components of the injector is contacted with a syringe. The syringe is moved along the longitudinal reference axis of the drive ram. This movement of the syringe along the longitudinal axis includes movement of the syringe along the sloping surfaces of the injectors first and second components. Due to the movement of the syringe along the longitudinal reference axis of the drive ram, each of the first and second components of the injector translate (e.g., unitarily move in a substantially straight line) away from one another.

Various refinements exist of the features noted in relation to the second aspect of the present invention. Further features may also be incorporated in the second aspect of the present invention as well. These refinements and additional features may exist individually or in any combination. The following portion of the summary pertains to this second aspect of the present invention.

The first and second components of the injector may translate in any appropriate orientation relative to the longitudinal reference axis of the drive ram. For instance, in some embodiments, the first and second components may translate in a plane (or a line for that matter) that is substantially perpendicular to the longitudinal reference axis.

The translation of the first and second components of the injector may be facilitated by or may be opposed by one or more forces. For instance, in some embodiments, the first and second components translate in opposition to a spring force that urges the first and second components toward one another.

In some embodiments, the first and second components may automatically move toward one another after they translate away from one another. This automatic movement may be due to continued movement of syringe along the longitudinal reference axis of the drive ram. Moreover, this automatic movement may be accomplished due to spring forces biasing the first and second components toward one another. So, for instance, pushing a syringe into the injector may initially cause the first and second components to separate from one another. However, the first and second components may move closer to one another after and/or as a result of the syringe being pushed into the injector to a particular extent (e.g., after and/or as a result of a radially outward-extending flange of the syringe clearing the first and second components).

In some embodiments of the method, the relative positions of the first and second components may be selectively (e.g., when a user desires) locked relative to the longitudinal reference axis. For example, the first and second components may be locked while a syringe is located between them (e.g., to assist in maintaining a position of the syringe relative to the injector).

Any appropriate medical fluid may be expelled from the syringe using the injector. For instance, the injector may be utilized to expel contrast media, saline, or a combination thereof from the syringe for a medical imaging procedure (e.g., CT imaging procedure, MRI procedure, ultrasound imaging procedure, optical imaging procedure, PET imaging procedure, SPECT imaging procedure, or the like.)

Again, the brief summary presented above is intended only to familiarize the reader with certain aspects and contexts of the present invention without limitation to the claimed subject matter.

BRIEF DESCRIPTION OF THE FIGURES

Various features, aspects, and advantages of the present invention may become better understood when the following detailed description is read with reference to the accompanying figures in which like characters represent like parts throughout the figures, wherein.

DETAILED DESCRIPTION OF SPECIFIC EMBODIMENTS

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a", "an", "the", and "said" are intended to mean that there are one or more of the elements. The terms "comprising", "including", and "having" are intended to be inclusive and mean that there may be additional elements other than the listed elements. Moreover, the use of "top", "bottom", "above", "below" and variations of these terms is made for convenience, but does not require any particular orientation of the components.

Figure 1:
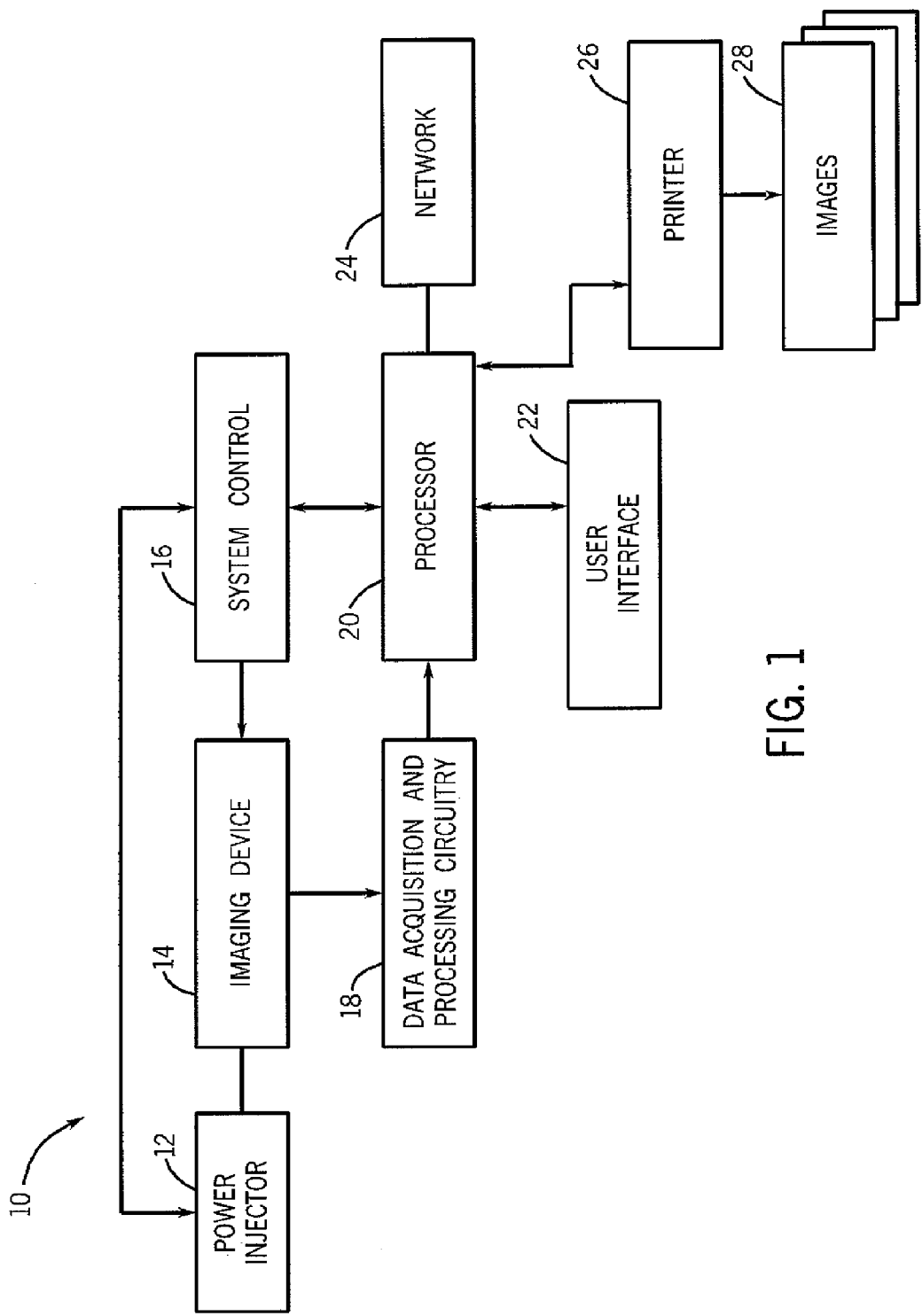
FIG. 1 is a block diagram of an imaging system.

Referring to FIG. 1, an imaging system 10 includes a power injector 12 adapted to inject medical fluid from a syringe and/or a plurality of syringes loaded onto power injector 12. The medical fluid may include a drug, contrast media, a radiopharmaceutical, saline solution, or a combination thereof. As will be described further below, power injector 12 may include a power head having one or more syringe mounts (e.g., 200 of FIGS. 4-8) adapted to securely and aptly retain syringes to the power head.

In certain embodiments, the syringe mount may include a base having a pair of retaining members operatively coupled to a lock, as generally described below with reference to FIGS. 4-8. For example, the retaining members may open and close about a portion (e.g., an end flange) of a syringe in response to movement of the syringe toward the base via engagement of the syringe with the retaining members. The retaining members may include tapered engagement portions that cause the arms to translate (e.g., move linearly) away from one another in opposite directions that are crosswise (e.g., perpendicular) to an engagement direction of the syringe with the retaining members. The retaining members may define a receptacle to capture the portion (e.g., end flange) of the syringe upon sufficient movement between and/or through the retaining members. In certain embodiments, the arms may automatically close onto, and capture, the portion (e.g., end flange) of the syringe via a spring or another biasing feature. For example, one or more springs may pull the retaining members inwardly toward one another after the portion of the syringe passes the tapered engagement portions of the retaining members.

Furthermore, the lock may secure the retaining members in a closed position about the portion (e.g., end flange) of the syringe, such that the retaining members cannot move out of the closed position into an open position. The lock may include a lever disposed on the base, although other actuators may be used to control the lock. The user may use the lever (see below) to lock the retaining members so as to prevent their movement.

In these embodiments, as discussed below, a user may press the syringe against portions of the syringe mount and mount the syringe single-handedly to the power injector due to automatic movement of the retaining members, and the user may subsequently lock the retaining members with a single hand as well. Thus, the user may single-handedly lock the retaining members after single handedly pressing the syringe until the retaining members close on the syringe. These features, and others, promote the power head 12 injecting medical fluid efficiently and properly, such as prescribed by a user or a healthcare provider. Further, syringe mounts described herein may be adapted to provide a user with convenient methods for loading or unloading syringes onto or from power injector 12. That is, the syringe mount may be designed in a manner conforming to the user's desires, thereby simplifying the overall process of coupling/decoupling syringes to or from power head/injector 12.

Continuing with FIG. 1, imaging system 10 includes an imaging device 14, a system control (e.g., control panel) 16, data acquisition and processing circuitry 18, a processor 20, a user interface 22, and a network 24. In the illustrated embodiment, the power injector 12 is coupled to the imaging device 14 and system control 16. Specifically, the imaging device 14 is configured to obtain signals representative of an image of a subject after the medical fluid (e.g., contrast media or radiopharmaceutical) has been administered to the subject via the power injector 12. The imaging system 10 may include a positron emission tomography (PET) system, a single photon emission computer tomography (SPECT) system, a nuclear medicine gamma ray camera, a magnetic resonance imaging (MRI) system, a computerized tomography (CT) imaging system, an optical imaging system, an ultrasound imaging system, or another suitable imaging modality. Image data indicative of regions of interest in a subject may be created by the imaging device 14 either in a conventional support, such as photographic film, or in a digital medium. As will be appreciated by those having ordinary skill in the art, imaging system 10 may be used to image a region of interest (e.g., organ(s) and/or other tissue(s)) at least partially based on concentrations of a medical fluid injected into a subject/patient by a syringe.

The system control 16 may include a wide range of circuits, such as imaging (e.g., radiation) source control circuits, timing circuits, circuits for coordinating data acquisition in conjunction with patient or table movements, circuits for controlling the position of imaging (e.g., radiation) detectors, and so forth. The imaging device 14, following acquisition of the image data or signals, may process the signals, such as for conversion to digital values, and forward the image data to data acquisition circuitry 18. In the case of analog media, such as photographic film, the data acquisition system may generally include supports for the film, as well as equipment for developing the film and producing hard copies that may be subsequently digitized. For digital systems, the data acquisition circuitry 18 may perform a wide range of initial processing functions, such as adjustment of digital dynamic ranges, smoothing or sharpening of data, as well as compiling of data streams and files, where desired. The data is then transferred to the processor 20 where additional processing and analysis is performed. For conventional media such as photographic film, the processor 20 may apply textual information to films, as well as attach certain notes or patient-identifying information. In a digital imaging system, the data processing circuitry may perform substantial analyses of data, ordering of data, sharpening, smoothing, feature recognition, and so forth.

Ultimately, the image data may be forwarded to an operator/user interface 22 for viewing and analysis. While operations may be performed on the image data prior to viewing, the operator interface 22 is at some point useful for viewing reconstructed images based upon the image data collected. In the case of photographic film, images may be posted on light boxes or similar displays to permit radiologists and attending physicians to more easily read and annotate image sequences. The image data can also be transferred to remote locations, such as via a network 24. In addition, the operator interface 22 may enable control of the imaging system, e.g., by interfacing with the system control 16. Furthermore, the imaging system 10 may include a printer 26 to output a hard copy of images 28. While FIG. 1 shows an example of one imaging system 10, it should be noted that principles of the invention apply to any imaging system utilizing an injector that includes or should include a syringe mount. Further, while FIG. 2 shows an exemplary injector 12, it should be noted that principles of the invention apply to any medical fluid injector that includes or should include a syringe mount.

Figure 2:
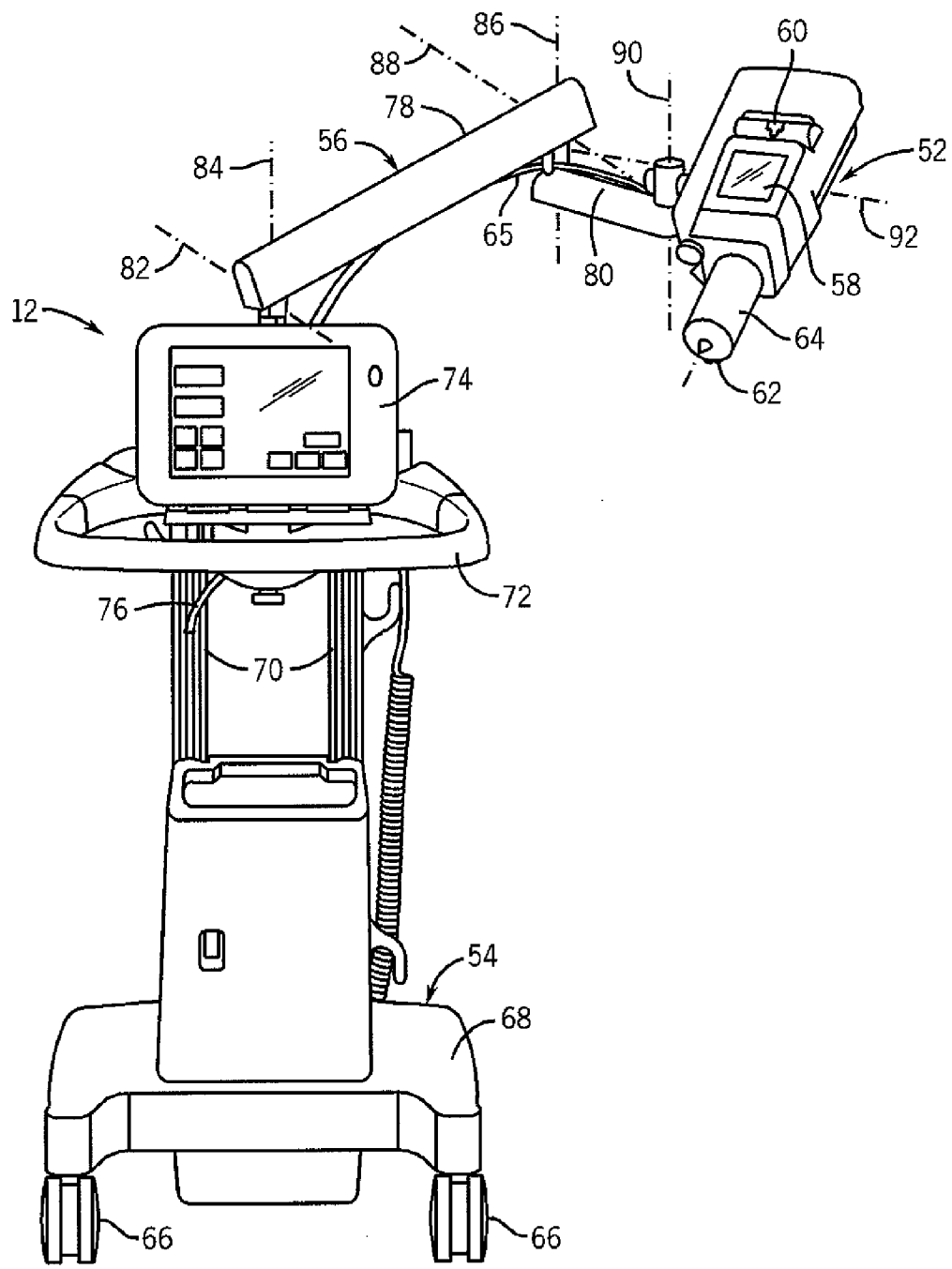
FIG. 2 is a perspective view of a power injector.

Referring to FIG. 2, the power injector 12 may include a power head 52, a stand assembly 54 and a support arm 56. The power head 52 may include a syringe mount adapted to aptly capture a syringe containing a medical fluid. For example, such a mounting system may provide optimal fluid injection parameters, such as pressure provided by the power head's ram to the syringe's plunger, for injecting fluid at a desired rate. As mentioned above, syringe mount(s) included with the power head 52 may be adapted to simplify tasks associated with loading syringes onto the power head 52, which may further enable the clinician to attend to additional tasks associated with other aspects of the injection procedure. The power head 52 may further include a display 58, a fluid control bar 60, and an air detector 62. The fluid control bar 60 may facilitate manual manipulation of a plunger in a syringe 64 mounted to the power head 52. The air detector 62 may signal a controller, such as controller 16 (FIG. 1) when air is detected in or leaving syringe 64.

The illustrated stand assembly 54 includes a set of four wheels 66, a chassis 68, vertical supports 70, a handle 72, and a display 74. The vertical supports 70 may adjustably elevate the handle 72, display 74, and the support arm 56 above chassis 68, and, in certain embodiments, it may have a recessed portion through which the power cable 76 is routed. The display 74 may include a liquid crystal display, a cathode ray tube display, an organic light emitting diode display, a surface emission display, or other appropriate display. The support arm 56 of the injector 12 shown in FIG. 2 includes multi-axis articulating members 78, 80. The illustrated articulating the member 78 has two degrees of freedom relative to the chassis 68 due to two perpendicular axes of rotation 82, 84. Similarly, exemplary the articulating member 80 has two degrees of freedom relative to the articulating member 78 by virtue of two perpendicular axes of rotation 86, 88. The power cable 76 is shown as being routed along the articulating the members 78, 80 to the power head 52.

The power head 52 of FIG. 2 may couple to the articulating member 80 via a joint that provides two degrees of freedom relative to the articulating member 80. As a result, in the present embodiment, the power head 52 may rotate about the axes 90, 92. In total, the illustrated power head 52 has six degrees of freedom relative to the chassis 68. Other embodiments may include more or fewer degrees of freedom.

Figure 3:
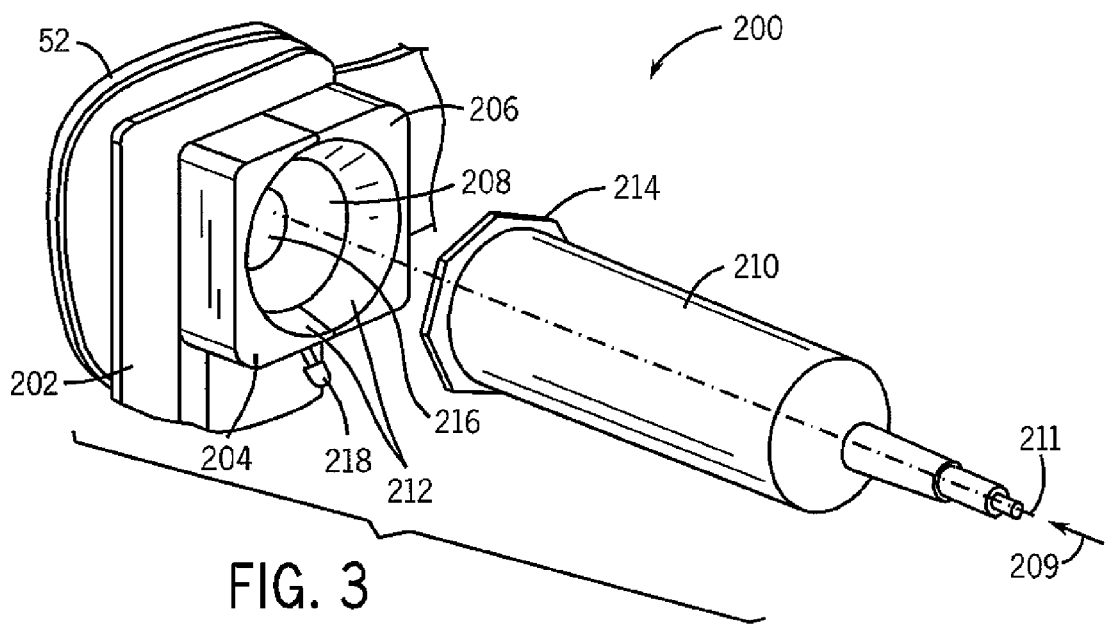
FIG. 3 is a perspective view of a syringe mount.

FIG. 3 is a perspective view of an embodiment of a syringe mount 200. The syringe mount 200 includes a base 202 coupled to a power head, such as the power head 52 shown by FIG. 2. While the base 202 may be an integral part of the power head 52 in some embodiments, the base 202 is shown as being removably attached to the power head 52 (e.g., as a component of a face plate). In the case of the syringe mount 200 being a face plate, the base 202 may include a latch mount having one or more latches that engage with mating latches of the power head 52. Other appropriate manners of engaging a face plate with a power head could also be appropriate. Syringe mount 200 further includes a plurality of syringe retainer components 204, 206. As discussed below, the retainer components 204, 206 may be movable along (e.g., parallel to) a surface of the base 202 in response to movement of the syringe 210 or upon receipt of the syringe 210 toward the base 202, thereby enabling the syringe 210 to be captured between the retainer components 204, 206.

The retainer components 204, 206 may come in direct contact with one another to effectively form a single structure, which exhibits an outer shape that is substantially rectangular and an inner shape that substantially conforms to a perimeter shape of a barrel of the syringe 210 (e.g., the inner shape of the single structure may be substantially circular). As an example of the inner shape, the movable retainer components 204, 206 may be disposed adjacent one another to define an aperture 208 adapted to receive syringe 210 in a direction 209 along a longitudinal axis 211 of the syringe 210. The aperture 208 may be adapted to align a plunger of the syringe 210 with a drive ram 216 of the power head/injector 52, wherein the drive ram 216 moves linearly along the longitudinal axis 211. In the illustrated embodiment, the longitudinal axis 211 may be oriented generally outward (e.g., perpendicular) from the base 202, and the retainer components 204, 206 may be movable generally crosswise (e.g., perpendicular) relative to the longitudinal axis 211. Specifically, the retainer components 204, 206, are disposed opposite to one another about the longitudinal axis 211 of the drive ram 216, such that the retainer components 204, 206 open and close at least generally toward and away from the longitudinal axis 211. As the retainer components 204, 206 close about the syringe 210, the geometry of the aperture 208 preferably assists in aligning the syringe 210 with the longitudinal axis 211 and the associated drive ram 216.

Each of the retainer components 204, 206 includes a sloped inner surface 212, which is tapered or sloped along the interior portion of the aperture 208 toward the longitudinal axis 211. As such, a size of a perimeter of the aperture 208 toward the exterior of the syringe mount 200 is generally greater than a size of the perimeter of the aperture at a more interior location thereof. The inner surfaces 212 of the retainer components 204, 206, collectively, may cause the aperture 208 to exhibit an at least generally conical shape, which is adapted to receive the syringe 210 in a sort of wedging manner (e.g., serves to part, split, divide). More specifically, the aperture 208 tends to narrow in diameter along the longitudinal axis 211 toward the base 202 (e.g., defining a cone-like shape that converges toward the base 202), such that receipt of the syringe 210 into the first conical aperture 208 causes the retainer components 204, 206 to translate apart from one another. In other words, the syringe 210 initially engages the surfaces 212 of the retainer components 204, 206, such that movement of the syringe 210 toward the base 202 in the direction 209 along the longitudinal axis 211 of a drive ram 216 forces the retainer components 204, 206 to translate (e.g. linearly move without rotation) away from one another and away from the longitudinal axis 211.

In some embodiments, the surfaces 212 may define a plurality of tapered portions (e.g. first and second tapered portions) one after another along the longitudinal axis 211 toward the base 202. In turn, these tapered portions may define a plurality of conical apertures (e.g., first and second conical apertures 208) one after another along the longitudinal axis 211 toward the base 202. The first tapered portions defined by the surfaces 212 may represent front engagement portions (e.g., tapered syringe interfaces), which directly contact the syringe 210 as the syringe 210 initially moves toward the retainer components 204, 206. Again, the first tapered portions may be adapted to wedge or bias the retainer components 204, 206 to translate outwardly from one another as the syringe moves toward base 202 and slides along the surfaces 212. The second tapered portions, which may follow the first tapered portions in the direction 209 toward the base 202, converge toward one another toward the base 209. Thus, the second conical aperture defined by the second tapered portions mirrors the first conical aperture 208 (i.e., diverging rather than converging toward the base 202). The second tapered portions enable the retainer components 204, 206 to close gradually toward one another after the syringe 210 passes the first tapered portions and continues to move toward the base 202. More specifically, as the syringe 210 moves along the second tapered portions toward the base 202, the retainer components 204, 206 are able to translate toward one another due to the diverging nature of the second tapered portions.

The movable retainer components 204, 206 may be biased (e.g., via a spring) such that the retainer components automatically translate (e.g., move linearly without rotation) toward and/or away from the longitudinal axis 211, as a user loads the syringe 210 onto the syringe mount 200. In other words, the movable retainer components 204, 206 are biased (e.g., via a spring) toward the longitudinal axis 211 of the drive ram 216. For example, the movable retainer components 204, 206 may be biased toward one another (e.g., spring-biased to close or converge toward one another), such that the retainer components 204, 206 are disposed in a normally closed position. In other words, the retainer components 204, 206 may be coupled to a spring loaded mechanism adapted to provide a biasing force which may counter forces applied by the user as the syringe 210 is inserted into the aperture 208. In this manner, the retainer components 204, 206 may automatically open as the syringe 210 initially engages and moves along the first tapered portions (e.g., surfaces 212), thereby forcing the retainer components 204, 206 to translate apart from one another against the biasing force. Subsequently, after passing the first tapered portions and reaching the second tapered portions, the inward biasing force (e.g., provided by a spring) may cause the retainer components 204, 206 to translate toward one another to close about the syringe 210. Thus, the biasing force may automatically close the retainer components 204, 206 about the syringe 210. In this manner, the retainer components 204, 206 move automatically inward relative to one another. In other words, manual insertion of the syringe 210 into the retainer components 204, 206 may impart an outward radial force to cause the retainer components 204, 206 to translate open, whereas the spring loaded mechanism may impart an inward radial force to cause the retainer components 204, 206 to automatically translate closed.

The syringe mount 200 is adapted to securely maintain the syringe 210, enabling the power head 52 to properly inject medical fluid from the syringe 210 to the patient. Accordingly, the syringe 210 includes a flange 214 disposed at the rear end of syringe 210, such that the retainer components 204, 206 can capture the flange 214 to retain the syringe 210 in a substantially fixed mounting position. As the user inserts the syringe 210 into the aperture 208, the flange 214 abuts the inner surfaces 212, causing the retainer components 204, 206 to gradually translate open in opposite directions away from one another as the syringe 210 moves in the direction 209. This enlarges and adapts aperture 208 for receiving the syringe 210. As mentioned above, the retainer components 204, 206 may be biased in opposite directions (e.g., inward) relative to one another by a suitable biasing feature, which opposes the initial expansion or translation apart of the retainer components 204, 206 during insertion. However, the user may insert the syringe 210 well within the aperture 208 so that the flange 214 is captured within a receptacle (e.g., 328 of FIGS. 6-7) disposed behind the retainer components 204, 206 as the biasing force causes the retainer components 204, 206 to translate together, thereby securing and aligning the syringe 210 with the ram 216. For example, the retainer components 204, 206 may automatically close about syringe 210 (e.g., via spring) upon reaching the receptacle behind the retainer components 204, 206, thereby holding the syringe 210 and/or the flange 214 to deter undesired movement of the syringe 210 while also orienting the ram 216 and syringe 210 substantially coaxial with one another along longitudinal axis 211. This holding of the syringe 210 by the syringe mount 200 enables the ram 216 to apply a desired force on a plunger of the syringe 210 along the longitudinal axis 211 for producing sufficient pressure that efficiently expels the medical fluid from the syringe 210.

Figure 4:
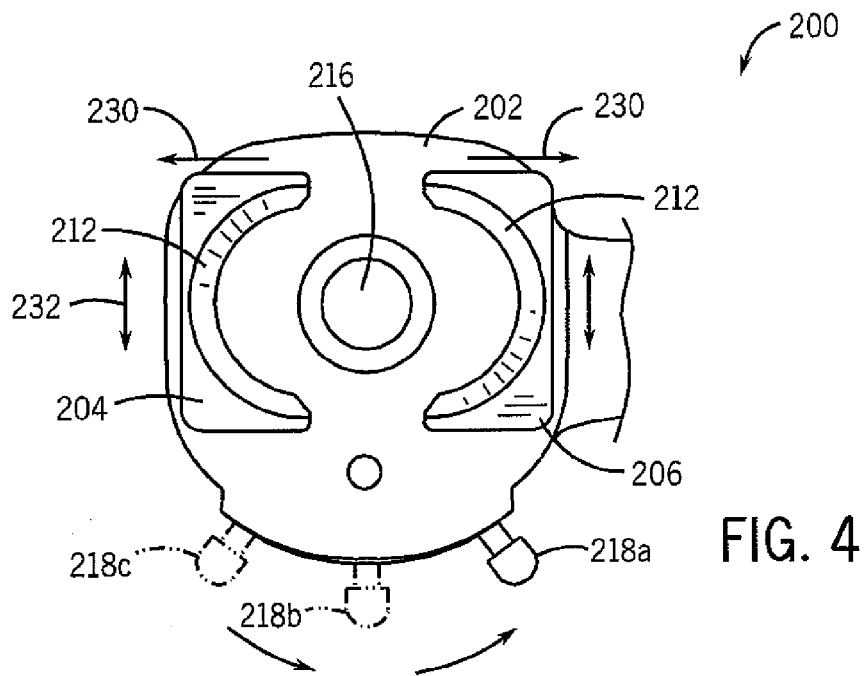
FIG. 4 is a front view of the syringe mount of FIG. 3.

As illustrated in FIG. 4, syringe mount 200 includes a Locking mechanism, which may include a lever 218, disposed beneath and adjacent to the retainer components 204, 206. Other embodiments of the syringe mount 200 may not include a locking mechanism or may include a locking mechanism exhibiting a different design and/or location. The locking mechanism is preferably designed to selectively (e.g., as a user desires) prevent undesired movement of the retainer components 204, 206 (e.g., while the retainer components 204, 206 are disposed in the closed position). The lever 218 is disposed on the base 202 and may be actuated (e.g., in a first direction) to secure and lock the retainer components 204, 206 in a closed position about the syringe. For example, after the user inserts and secures the syringe 210 within the aperture 208, the user may thereafter move the lever 218 so as to lock the retainer components 204, 206 into place. In so doing, the locking mechanism may promote the retainer components 204, 206 remaining snuggly secured around the syringe 210 after the retainer components 204, 206 move inward to hold the syringe 210. As discussed further below, the locking functionality provided by the locking mechanism may prevent the retainer components 204, 206 from opening or otherwise loosening once the syringe 210 is captured within the aperture 208. The locking mechanism may provide additional functionalities pertinent to alignment of the syringe 210 with the ram 216 of the power head 52 for achieving desirable injection output from the syringe 210.

Referring to FIG. 4, the movable retainer components 204, 206 are in an open position, whereby the retainer components 204, 206 are disposed away from one another. In the illustrated embodiment, the retainer components 204, 206 are separated from one another so as to enlarge the aperture 208, thereby permitting the user to insert the syringe 210 adjacent to the ram 216. As mentioned above, this open configuration may be achieved automatically when the user inserts the syringe 210 within the aperture 208. Alternatively, the user operate the locking mechanism to open the arms 204 206. For example, this opening may be accomplished by moving the lever 218 of the locking mechanism from a closed position 218c, via position 218b, to position 218a. As illustrated by arrows 230, the aforementioned movement of the lever 218 may cause the movable retainer components 204, 206 to translate outward in opposite directions to an open position. Arrows 230 are shown to represent linear movement of the retainer components 204, 206 in opposite outward directions that are crosswise (e.g., perpendicular) to the longitudinal axis 211. This enlarges the aperture 208, thereby enabling the user to either insert and install the syringe 210 or release and remove the syringe 210 from syringe mount 200.

Figure 5:
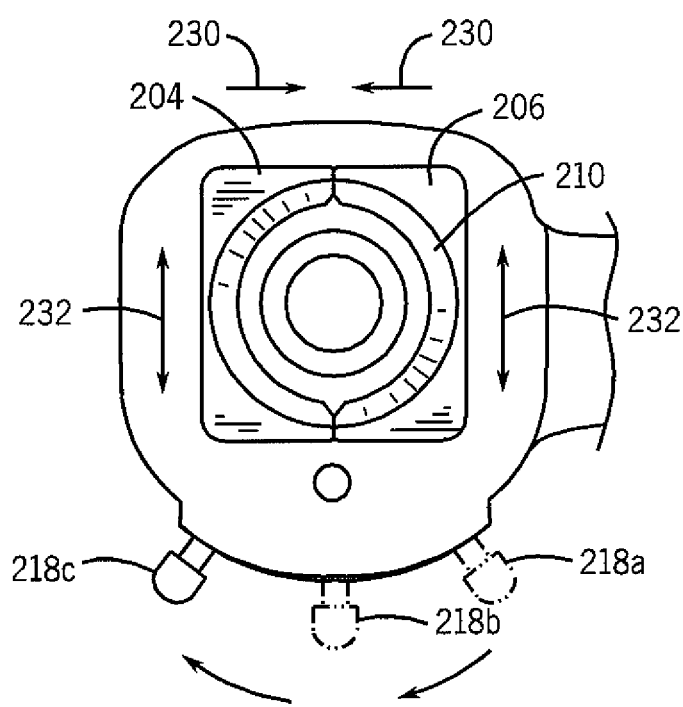
FIG. 5 is a front view of a syringe coupled to the syringe mount of FIG. 3.

FIG. 5 shows the syringe mount 200 in a closed position, whereby the retainer components 204, 206 snuggly fit around and maintain the syringe 210 in place. As mentioned above, after the user inserts the syringe 210 into the aperture 208, the retainer components 204, 206 translate outward to open and, thereafter, translate inward to close and retain the syringe 210 in place. In order to lock the retainer components 204, 206 and to thereby reduce the likelihood of the syringe mount 200 opening at an undesired time, the user may move the lever 218 of the locking mechanism from the open position 218a, via position 218b, to the closed position 218c. This promotes the retainer components 204, 206 remaining locked in the closed position. In other words, the closed position 218c of lever 218 enables the locking mechanism to deter movement of the retainer components 204, 206, such that the retainer components 204, 206 cannot inadvertently move, loosen, or generally release syringe 210 at an undesired time (e.g., during an injection procedure). The locking function provided by the locking mechanism may promote the aperture 208 maintaining an appropriate size that corresponds to the size of syringe 210. This may deter the syringe 210 from wiggling or otherwise loosening within the aperture 208 or experiencing undesired movements that may cause the syringe 210 to be displaced from the syringe mount 200.

While the aforementioned locking mechanism may be utilized to lock and/or move the retainer components 204, 206 in lateral direction (as shown by arrows 230), the locking mechanism of some embodiments may also move the retainer components 204, 206 in a vertical direction, as shown by arrows 232. For example, while movement of the lever 218 from the position 218a to the position 218b may lock or unlock the movable retainer components 204, 206, movement of the lever 218 from the position 218b to the position 218c may cause the retainer components 204, 206 to vertically reposition the syringe 210 within the aperture 208. That is, after the retainer components 204, 206 have engaged the syringe 210 to hold the same in place (e.g., due to initial movement of lever 218), further movement of lever 218 may impart vertical movement of the retainer components 204, 206 to align and/or engage the syringe 210 with the ram 216. In an exemplary embodiment, movement of the lever 218 from the position 218b to 218c may cause move the retainer components 204, 206 downward, so as to align and engage the plunger of syringe 210 with the ram 216 along the longitudinal axis 211.

Still some embodiments, movement of the lever 218 may be partitioned, such that portions of the movement may impart downward motion onto the retainer components 204, 206, while other portions of the lever's movement may impart upward motion to the retainer components 204, 206. This may provide the user with ability to fine tune the positioning of the syringe 210 with the ram 216 after the retainer components 204, 206 are closed about the barrel of the syringe. Alignment of the syringe 210 with the ram 216 is desirable because it promotes the ram 216 applying appropriate pressure on the plunger of the syringe 210 for achieving optimal fluid injection from the syringe 210. As such, the ram 216 may be utilized to drive and output fluid (e.g., radiopharmaceutical, contrast media, saline, etc.) through the syringe 210 while the syringe 210 is captured by the retainer components 204, 206.

After the injection operation is complete, the user may move the lever 218 from the position 218c to the position 218b, thereby releasing the grip applied by the retainer components 204, 206 on syringe 210. This initial unlocking operation may disengage and move the syringe 210 out of alignment with the ram 216. The above-mentioned intermittent unlocking operation may loosen-up the syringe 210 within the aperture 208 while ensuring that the injection operation terminates. Hence, the syringe 210 may remain held by the retainer components 204, 206 giving the user an opportunity to properly complete any post-injection procedures. For example, the user may want to manipulate (e.g., remove) any tubes, connectors, valves, catheters and/or the like coupled to the syringe 210 and/or to the patient. In addition, the intermittent unlocking operation may slightly dislodge the syringe 210 from aperture 208, so that the user may apply a minimal force to remove the syringe 210 completely from the syringe mount 200. Thus, the user may gently remove the syringe 210 while avoiding the use of excessive force.

Hence, in some embodiments, the loading and/or unloading process of the syringe 210 onto the syringe mount 200 may involve two main stages. For example, in loading the syringe 210 onto the mounting system 200, the first stage may be completed when the user first inserts the syringe within the aperture 208 until the syringe 210 is securely gripped or held by the movable retainer components 204, 206. In the second stage of the loading process, the user may lock the position of the retainer components 204, 206 by actuating the lever 218, as indicated above. In between the two aforementioned stages, the syringe 210 may be retained indefinitely by the retainer components 204, 206, enabling the user to perform additional tasks before locking the syringe 210 to the mounting system 200. The locking operation may further promote the syringe 210 being properly engaged with the ram 216 for promoting proper injection of contrast fluid from the syringe 210.

Figure 6:
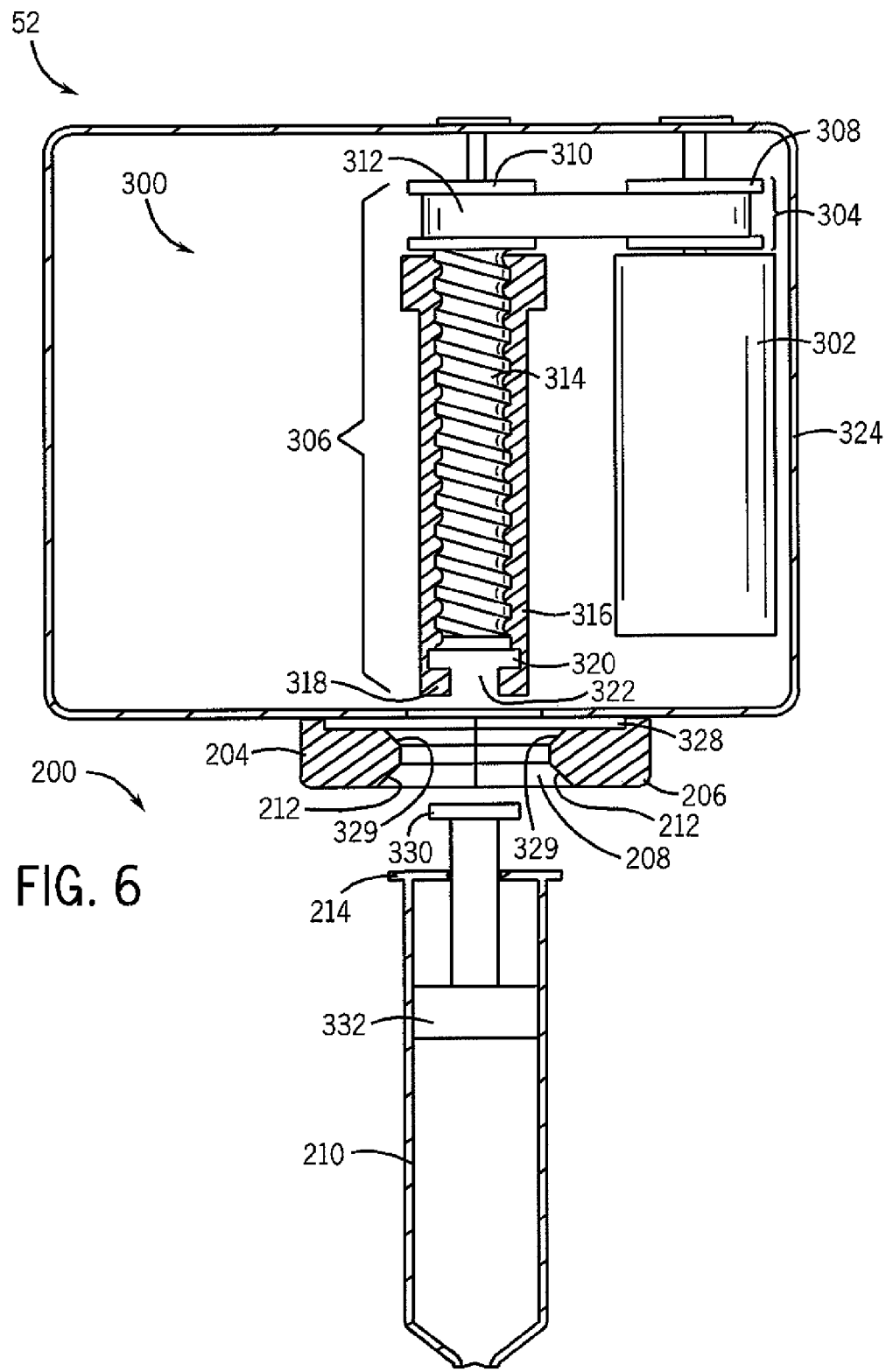
FIG. 6 is top cross section of a syringe mount coupled to a syringe drive of a power head.

FIG. 6 illustrates a syringe mount coupled to an exemplary syringe drive in accordance with certain embodiments. Accordingly, the syringe mount 200 is coupled to a syringe drive 300, such as a syringe drive included in the power head 52. The syringe drive 300 may include an electric motor 302, a transmission 304, and a linear drive 306. The electric motor 302 may be a DC electric motor or an AC electric motor, such as a stepper motor. The transmission 304 may include a primary pulley 308, a secondary pulley 310, and a belt 312. The linear drive 306 may include an externally threaded shaft, worm, or screw 314, an outer shaft 316, and a syringe interface 318. Transmission 304 may be a reducing transmission. For example, the ratio of the diameter of the secondary pulley 310 to the diameter of the primary pulley 308 may be greater than 1.5:1, greater than 2:1, greater than 3:1, greater than 4:1, greater than 5:1, greater than 8:1, greater than 20:1, or more. The syringe interface 318 includes a wider, outer-end receptacle 320 and a shaft slot 322. Other embodiments may include another appropriate syringe interface 318. In some embodiments, one or more of the motor 302, the transmission 304, and the drive 306 may be substantially or entirely non-ferrous. In some embodiments, one or more of the motor 302, transmission 304, and drive 306 may be partially, substantially, or entirely shielded by shielding 324. As further illustrated by FIG. 6, the syringe mount 200 is coupled to the shielding 324. This coupling may be permanent or it may be temporary, in which case the syringe mount 200 may latch onto the shielding 324 via a fastening and or locking mechanism. As such, the syringe mount 200 may be coupled with power heads of various kinds.

As further illustrated, the syringe mount 200 includes a receptacle 328 having tapered ends 329 adapted to receive the flange 214 of the syringe 210. During mounting of the syringe 210, the user may urge (e.g., push) an end portion of the syringe 210 against the tapered portions 212 of the retainer components 204, 206. This causes the retainer components 204, 206 to translate in opposite linear directions until the flange 214 is positioned within the receptacle 328, which allows the syringe 210 to be located in proximity to the syringe interface 318. During the insertion of the syringe 210 into the aperture 208, the flange 214 may press against the surfaces 212 so as to move and open the retainer components 204, 206 until the flange 214 enters the receptacle 328 via the tapered ends 329. As the flange 214 enters the receptacle 328, the retainer components 204, 206 are biased (e.g., via a spring) inwardly toward one another, thereby causing the retainer components 204, 206 to automatically translate closed about the flange 214 such that the flange 214 is retained in the receptacle 328. In other words, when pressing the syringe 210 toward the base 202, the flange 214 of the syringe 210 enters into the receptacle 328 disposed beyond a front portion of the retainer components 204, 206. The, using a single hand, the user may press the syringe 210 against the retainer components 204, 206 to an extent sufficient to move the syringe into the aperture 208 so that the retainer components 204, 206 automatically close about the syringe 210. During the insertion process, the user may insert the button 330 of the syringe plunger 332 through the aperture 208, and place the plunger within the outer-end receptacle 320 of the syringe interface 318, as further illustrated in FIG. 7. Thereafter, the user may lock the retainer components 204, 206 in a closed position about the syringe 210.

Figure 7:
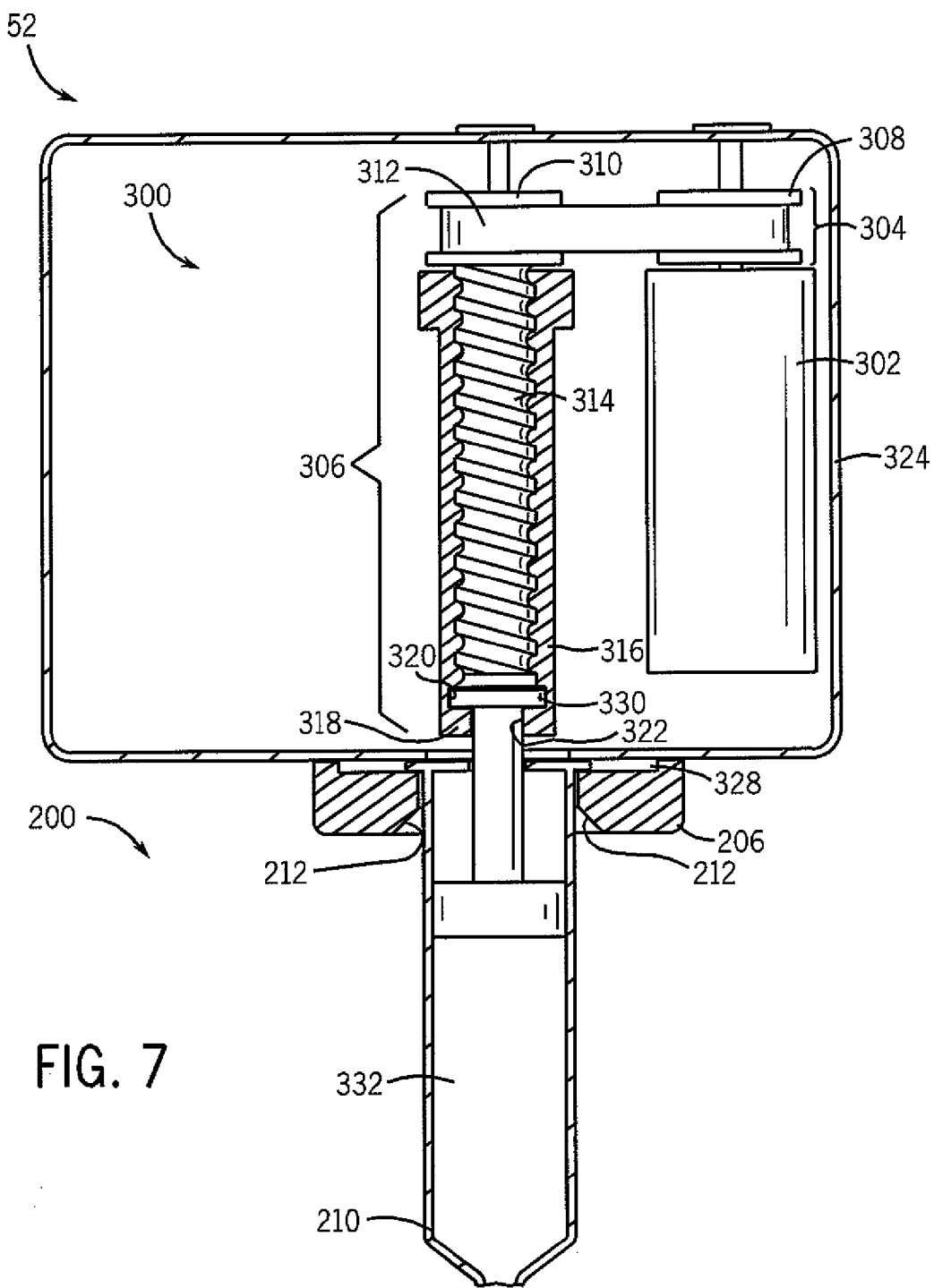
FIG. 7 is a top cross section of the syringe coupled to the syringe mount of FIG. 6.

FIG. 7 illustrates the syringe 210 coupled to the mounting system 200 and the syringe drive 300, in accordance with certain embodiments. In the illustrated embodiment, the button 330 is fully placed within the syringe interface 318, such that the upper surface of the plunger 332 (or its drive shaft) abuts against the screw drive 316. Hence, in operation, the electric motor 302 of the syringe drive 300 drives the primary pulley 308. As the primary pulley 308 rotates, the belt 312 rotates the secondary pulley 310. The rotation of the secondary pulley 310 drives the screw 314, which rotates within the outer shaft 316. The outer shaft 316 is threaded so that rotation of the screw 314 applies a linear force to the outer shaft 316. As the screw 314 rotates, the outer shaft 316 may be pulled outward by the screw 314. Hence, the outer shaft 316 may translate (e.g., move linearly) relative to the screw 314 and move the plunger 332 of the syringe 210 via the syringe interface 318. Again, the retainer components 204, 206 and lever 218 may promote the syringe 210 remaining secured in a desired alignment with the syringe drive 300 and, more specifically, the syringe interface 318.

Figure 8:
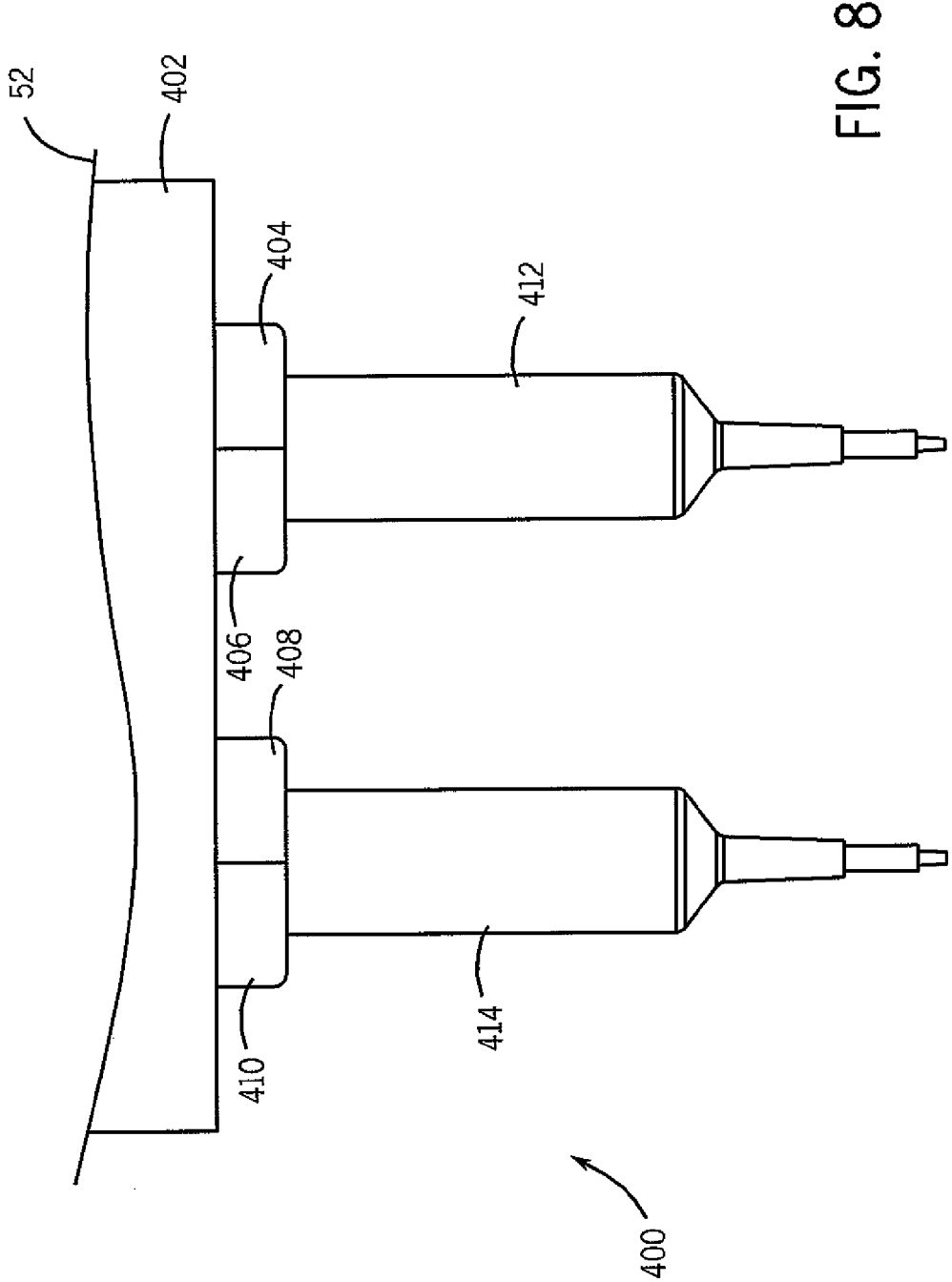
FIG. 8 is a top view of a dual head syringe mount.

FIG. 8 illustrates an embodiment of a dual head syringe mount 400 having certain features as discussed in detail above. Syringe mount 400 may include any of the features of the syringe mounts 200 discussed above. While the present embodiment illustrates a mounting system adapted to accommodate two syringes, other embodiments may be envisioned to more than two syringes. The mounting system 400 and those accommodating multiple syringes may be desirable for use in various settings, such as those desiring simultaneous or sequential injection of medical fluids. To accommodate such settings, the power head 52 may be configured to inject medical fluids from each of the syringes 412, 414 independently. For example, the power head 52 may include multiple rams, whereby each ram may be configured to apply a desired amount of pressure to each of the plungers of the syringes 412, 414, as prescribed by the user. In so doing, the user may control injection rate of each medical fluid contained within the syringes 412, 414.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A front-loading, contrast media injector comprising:
an injector housing having an opening defined therein;
a drive ram, at least a portion of which is movable into and out of the injector housing along a longitudinal reference axis of the drive ram through the opening in the injector housing; and
a syringe mount coupled to the injector housing and comprising a plurality of retainer components, wherein the plurality of retainer components collectively define a syringe-receiving aperture that is aligned with the opening in the injector housing, wherein each the plurality of retainer components are disposed about an exterior of a syringe and are in position to restrain movement of a syringe away from the injector housing when the syringe is installed on the contrast media injector and as the drive ram is advanced in the direction of the syringe, wherein each of the retainer components comprises a sloped surface that defines a perimeter portion of the syringe-receiving aperture, wherein the sloped surface of each of the retainer components projects in a direction of the longitudinal reference axis and projects toward the exterior of the syringe when installed on the contrast media injector using the syringe mount, wherein the sloped surface of each of the retainer components slopes toward the longitudinal reference axis of the drive ram progressing along the longitudinal reference axis in the direction of the injector housing, wherein each of the retainer components translates linearly toward the longitudinal reference axis, wherein each of the retainer components translates linearly away from the longitudinal reference axis, wherein each of the retainer components is biased toward the longitudinal reference axis, wherein the plurality of retainer components comprises first and second retainer components, wherein the first and second retainer components each translate linearly toward the longitudinal reference axis to both reduce a spacing between the first and second retainer components and to reduce a size of the syringe-receiving aperture, wherein the first and second retainer components each translate linearly away from the longitudinal reference axis to both increase the spacing between the first and second retainer components and to increase the size of the syringe-receiving aperture, and wherein the size of the syringe-receiving aperture is taken perpendicularly to the longitudinal reference axis.

2. The injector of claim 1, wherein each of the retainer components is spring-biased toward the longitudinal reference axis of the drive ram.

3. The injector of claim 1, wherein the longitudinal reference axis of the drive ram is interposed between and does not intersect either of the first and second retainer components.

4. The injector of claim 1, wherein each of the first and second retainer components comprises a C-clamp.

5. The injector of claim 1, wherein the sloped surface of each of the retainer components is designed to cause translation of the retainer components outwardly away from the longitudinal reference axis of the drive ram when a syringe is moved along the longitudinal reference axis toward the opening in the injector housing.

6. The injector of claim 1, wherein the sloped surface of each of the retainer components is designed to cause translation of the retainer components outwardly away from the longitudinal reference axis of the drive ram when a syringe is moved along the longitudinal reference axis into the opening in the injector housing.

7. The injector of claim 1, wherein the syringe-receiving aperture comprises a substantially conical aperture adapted to receive a syringe.

8. The injector of claim 1, wherein each of the plurality of retainer components has a receptacle defined therein to accommodate at least a portion of a flange of a syringe.

9. The injector of claim 1, further comprising a lock adapted to secure the plurality of retainer components in a desired position.

10. The injector of claim 9, wherein the lock comprises a lever.

11. The injector of claim 10, wherein the plurality of retainer components are separated from one another by a first distance when the lever is in a first position, and wherein the plurality of retainer components are separated from one another by a second distance greater than the first distance when the lever is in a second position different from the first position.

12. The injector of claim 1, wherein the syringe mount is a component of a removable face plate of the injector.

13. The injector of claim 1, wherein the syringe mount is substantially integral with the injector housing.

14. The injector of claim 1, wherein the syringe mount is a component of an adapter for at least temporarily making an original syringe mount of the injector compatible to accommodate a syringe that the original syringe mount was not originally designed to accommodate.

15. The injector of claim 1, further comprising a syringe disposed between the plurality of retainer components.

16. The injector of claim 15, further comprising contrast media, saline, or a combination thereof disposed within the syringe.

17. The injector of claim 1, wherein the sloped surface comprises a first tapered portion that slopes toward the longitudinal reference axis of the drive ram progressing along the longitudinal reference axis in the direction of the injector housing.

18. The injector of claim 17, wherein each of the retainer components further comprises a second tapered portion that slopes away from the longitudinal reference axis proceeding in the direction of the injector housing, and wherein each of the second tapered portions is located between the first tapered portion of the corresponding retainer component and the injector housing.

19. The injector of claim 17, wherein an interaction between a syringe and the sloped surface of each of the retainer components, while moving the syringe relative to the injector housing and along the longitudinal reference axis to install the syringe on the injector housing, linearly moves the retainer components away from the longitudinal reference axis.

20. A method of using a contrast media injector having a drive ram, at least a portion of which is movable into and out of an injector housing along a longitudinal reference axis of the drive ram, the method comprising:
   installing a syringe on the injector, wherein the installing comprises:
      contacting a sloping surface of each of first and second components of the injector with a syringe;
      moving the syringe along the longitudinal reference axis of the drive ram, wherein the moving comprises moving the syringe along the sloping surface of the first component during the contacting and moving the syringe along the sloping surface of the second component during the contacting;
      linearly translating an entirety of each of the first and second components of the injector both away from one another and away from the longitudinal reference axis, all due to the moving of the syringe along the longitudinal reference axis of the drive ram and the contacting of the syringe with the sloping surface of each of the first and second components; and
      automatically moving the first and second components in opposite linear directions so that the first and second components both move toward one another and toward the longitudinal reference axis, wherein the automatically moving occurs after the translating, due to continued moving of the syringe along the longitudinal reference axis of the drive ram, and disposes the first and second components about an exterior of the syringe in a position for the first and second components to restrain movement of the syringe away from the injector housing during movement of the drive ram in the direction of the syringe.

21. The method of claim 20, wherein the linearly translating occurs in a plane substantially perpendicular to the longitudinal reference axis.

22. The method of claim 20, wherein the linearly translating occurs in opposition to a spring force that urges the first and second components toward one another.

23. The method of claim 20, wherein the automatically moving is accomplished due to spring forces biasing the first and second components toward one another and toward the longitudinal reference axis.

24. The method of claim 20, further comprising selectively locking a position of the first and second components relative to the longitudinal reference axis.

25. The method of claim 24, wherein the selectively locking is performed after the moving of the syringe along the longitudinal reference axis of the drive ram and while the syringe is located between the first and second components of the injector.

26. The method of claim 20, further comprising:
   expelling contrast media, saline, or a combination thereof from the syringe using the injector.

27. The method of claim 20, wherein the moving the syringe along the sloping surface of the first component and second component occurs while the syringe remains in contact with the sloping surface of each of the first and second components.

* * * * *